(12) United States Patent
Yang et al.

(10) Patent No.: US 6,258,121 B1
(45) Date of Patent: Jul. 10, 2001

(54) STENT COATING

(75) Inventors: Dachuan Yang, Plymouth; Joel L. Stanslaski, New Hope; Lixiao Wang, Maple Grove; Scott R. Smith, Chaska, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/346,975

(22) Filed: Jul. 2, 1999

(51) Int. Cl.$^7$ ........................................................ A61F 2/06
(52) U.S. Cl. ........................ 623/1.46; 427/2.25; 427/2.21
(58) Field of Search .................... 623/1.46–1.48, 623/1.16, 1.42, 1.43, 1.38, 1.39, 1.4; 427/2.3

(56) References Cited

U.S. PATENT DOCUMENTS

| | | | |
|---|---|---|---|
| 3,663,288 | 5/1972 | Miller | 117/7 |
| 3,779,792 | 12/1973 | Stoy et al. | 117/72 |
| 4,047,957 | 9/1977 | De Winter et al. | 96/67 |
| 4,100,309 | 7/1978 | Micklus et al. | 427/2 |
| 4,119,094 | 10/1978 | Micklus et al. | 128/132 R |
| 4,263,188 | 4/1981 | Hampton et al. | 260/29.2 TN |
| 4,306,998 | 12/1981 | Wenzel et al. | 260/13 |
| 4,373,009 | 2/1983 | Winn | 428/424.2 |
| 4,387,024 | 6/1983 | Kurihara et al. | 210/490 |
| 4,391,797 | 7/1983 | Folkman et al. | 424/19 |

(List continued on next page.)

FOREIGN PATENT DOCUMENTS

| | | |
|---|---|---|
| 556350 A1 | 10/1983 | (AU) . |
| 556351 A1 | 10/1986 | (AU) . |
| 0 093 094 A1 | 11/1983 | (EP) . |
| 0 106 004 A1 | 4/1984 | (EP) . |
| 0 166 998 A2 | 1/1986 | (EP) . |
| 0 274 846 B1 | 7/1988 | (EP) . |
| 0 294 905 A1 | 12/1988 | (EP) . |
| 0 389 632 A1 | 10/1990 | (EP) . |
| 0 395 098 A1 | 10/1990 | (EP) . |
| 0 407 965 A1 | 1/1991 | (EP) . |

(List continued on next page.)

OTHER PUBLICATIONS

Jarr, E.M. et al., "Sustained Release of Lidocaine from an Injectable Implant System for Treatment of Post–Operative Pain," Proceed. Int'l. Symp. Control. Rel. Bioact. Mater., 26, (1999) pp. 631–632.

Bartoli et al., "In Vitro and In Vivo Antitumoral Activity of Free, and Encapsulated Taxol", *J. Microencapsulation*, vol. 7, No. 2 (1990) pp. 191–97.

Bruck, Stephen D., "Interactions of Synthetic and natural surfaces with blood in the Physiological Environment,", *J. Biomed. Mater. Res. Symposium*, No. 8 (1997) pp. 1–21.

Cohn, Daniel et al., "Biodegradable PEO/PLA Block Copolymers," *Journal of Biomedical Materials Research*, vol. 22, No. 11, Nov. 1988, pp. 993–1009.

(List continued on next page.)

*Primary Examiner*—David H. Willse
*Assistant Examiner*—Suzette J. Jackson
(74) *Attorney, Agent, or Firm*—Crompton, Seager & Tufte, LLC

(57) ABSTRACT

A stent having a polymeric coating for controllably releasing an included active agent. The polymeric coating includes a blend of a first polymeric material, which if alone, would release the agent at a first, higher rate, and a second polymeric material, which if alone would release the agent at a second, lower rate over a longer time period. One stent coating utilizes a faster releasing hydrophilic polymeric material and a slower releasing hydrophobic material. One stent coating includes a blend of a faster releasing PLA-PEO copolymer and a slower releasing PLA-PCL copolymer. One active agent is Taxol. One use of the Taxol delivering stent is to inhibit restenosis following angioplasty.

13 Claims, 2 Drawing Sheets

U.S. PATENT DOCUMENTS

| | | | |
|---|---|---|---|
| 4,459,317 | 7/1984 | Lambert | 427/2 |
| 4,487,808 | 12/1984 | Lambert | 428/423.1 |
| 4,492,622 | 1/1985 | Kuypers | 204/403 |
| 4,536,179 | 8/1985 | Anderson et al. | 604/266 |
| 4,548,844 | 10/1985 | Podell et al. | 428/35 |
| 4,642,267 | 2/1987 | Creasy et al. | 428/413 |
| 4,666,437 | 5/1987 | Lambert | 604/265 |
| 4,675,361 | 6/1987 | Ward, Jr. | 525/92 |
| 4,692,352 | 9/1987 | Huddleston | 427/208.4 |
| 4,705,709 | 11/1987 | Vailancourt | 428/36 |
| 4,721,117 | 1/1988 | Mar et al. | 128/772 |
| 4,734,092 | 3/1988 | Millerd | 604/67 |
| 4,748,986 | 6/1988 | Morrison et al. | 128/772 |
| 4,768,507 | 9/1988 | Fischell et al. | 128/303 R |
| 4,770,664 | 9/1988 | Gogolewski | 623/66 |
| 4,780,352 | 10/1988 | Palumbo | 428/138 |
| 4,833,014 | 5/1989 | Linder et al. | 428/308.4 |
| 4,841,976 | 6/1989 | Packard et al. | 128/657 |
| 4,867,173 | 9/1989 | Leoni | 128/772 |
| 4,876,126 | 10/1989 | Takemura et al. | 428/35.7 |
| 4,884,579 | 12/1989 | Engelson | 128/772 |
| 4,923,464 | 5/1990 | DiPisa, Jr. | 606/195 |
| 4,925,698 | 5/1990 | Klausner et al. | 427/2 |
| 4,943,460 | 7/1990 | Markle et al. | 428/36.9 |
| 4,959,074 | 9/1990 | Halpern et al. | 623/66 |
| 4,964,409 | 10/1990 | Tremulis | 128/657 |
| 4,969,890 | 11/1990 | Sugita et al. | 606/192 |
| 4,980,231 | 12/1990 | Baker et al. | 428/36.9 |
| 4,994,071 | 2/1991 | MacGregor | 606/194 |
| 5,002,582 | 3/1991 | Guire et al. | 623/66 |
| 5,007,928 | 4/1991 | Okamura et al. | 623/6 |
| 5,008,363 | 4/1991 | Mallon et al. | 528/49 |
| 5,019,096 | 5/1991 | Fox, Jr. et al. | 623/1 |
| 5,026,607 | 6/1991 | Kiezulas | 428/423.7 |
| 5,037,656 | 8/1991 | Pitt et al. | 424/443 |
| 5,037,677 | 8/1991 | Halpern et al. | 427/338 |
| 5,040,543 | 8/1991 | Badera et al. | 128/772 |
| 5,049,403 | 9/1991 | Larm et al. | 427/2 |
| 5,057,371 | 10/1991 | Canty et al. | 428/411.1 |
| 5,066,705 | 11/1991 | Wickert | 524/457 |
| 5,067,489 | 11/1991 | Lind | 128/772 |
| 5,069,217 | 12/1991 | Fleischhacker, Jr. | 128/657 |
| 5,069,226 | 12/1991 | Yamauchi et al. | 128/772 |
| 5,079,093 | 1/1992 | Akashi et al. | 428/441.1 |
| 5,080,683 | 1/1992 | Sulc et al. | 623/66 |
| 5,080,924 | 1/1992 | Kamel et al. | 427/2 |
| 5,084,315 | 1/1992 | Karimi et al. | 428/36.6 |
| 5,091,205 | 2/1992 | Fan | 427/2 |
| 5,092,885 | 3/1992 | Yamada et al. | 623/11 |
| 5,102,401 | 4/1992 | Lambert et al. | 604/264 |
| 5,102,402 | 4/1992 | Dror et al. | 604/265 |
| 5,102,417 | 4/1992 | Palmaz | 606/195 |
| 5,105,010 | 4/1992 | Sundararaman et al. | 564/252 |
| 5,107,852 | 4/1992 | Davidson et al. | 128/772 |
| 5,128,170 | 7/1992 | Matsuda et al. | 427/2 |
| 5,129,890 | 7/1992 | Bates et al. | 604/281 |
| 5,160,790 | 11/1992 | Elton | 428/412 |
| 5,211,183 | 5/1993 | Wilson | 128/772 |
| 5,213,111 | 5/1993 | Cook et al. | 128/772 |
| 5,217,026 | 6/1993 | Stoy et al. | 128/772 |
| 5,222,971 | 6/1993 | Willard et al. | 606/158 |
| 5,240,994 | 8/1993 | Brink et al. | 525/54.2 |
| 5,241,970 | 9/1993 | Johlin, Jr. et al. | 128/772 |
| 5,243,996 | 9/1993 | Hall | 128/772 |
| 5,250,613 | 10/1993 | Bergstrom et al. | 525/54.1 |
| 5,266,359 | 11/1993 | Spielvogel | 427/388.4 |
| 5,275,173 | 1/1994 | Samson et al. | 128/772 |
| 5,282,823 | 2/1994 | Schwartz et al. | 606/198 |
| 5,283,063 | 2/1994 | Freeman | 424/427 |
| 5,290,585 | 3/1994 | Elton | 427/2 |
| 5,304,121 | 4/1994 | Sahatjian | 604/53 |
| 5,304,140 | 4/1994 | Kugo et al. | 604/281 |
| 5,324,261 | 6/1994 | Amundson et al. | 604/96 |
| 5,370,614 | 12/1994 | Amundson et al. | 604/96 |
| 5,380,299 | 1/1995 | Fearnot et al. | 604/265 |
| 5,383,928 | 1/1995 | Scott et al. | 623/1 |
| 5,419,760 | 5/1995 | Narciso, Jr. | 604/8 |
| 5,423,885 | 6/1995 | Williams | 623/1 |
| 5,443,458 | 8/1995 | Eury | 604/891.1 |
| 5,443,496 | 8/1995 | Schwartz et al. | 623/1 |
| 5,447,724 | 9/1995 | Helmus et al. | 424/426 |
| 5,449,372 | 9/1995 | Schmaltz et al. | 606/198 |
| 5,449,382 | 9/1995 | Dayton | 623/1 |
| 5,464,650 | 11/1995 | Berg et al. | 427/2.3 |
| 5,470,829 | 11/1995 | Prisell et al. | 514/12 |
| 5,476,909 | 12/1995 | Kim et al. | 525/408 |
| 5,512,055 | 4/1996 | Domb et al. | 604/265 |
| 5,514,154 | 5/1996 | Lau et al. | 606/195 |
| 5,527,337 | 6/1996 | Stack et al. | 606/198 |
| 5,545,208 | 8/1996 | Wolff et al. | 623/1 |
| 5,548,035 | * 8/1996 | Kim et al. | 525/408 |
| 5,562,922 | 10/1996 | Lambert | 424/486 |
| 5,569,463 | 10/1996 | Helmus et al. | 424/426 |
| 5,576,072 | 11/1996 | Hostettler et al. | 427/532 |
| 5,578,075 | 11/1996 | Dayton | 623/1 |
| 5,591,227 | 1/1997 | Dinh et al. | 623/1 |
| 5,605,696 | 2/1997 | Eury et al. | 424/423 |
| 5,609,629 | 3/1997 | Fearnot et al. | 623/1 |
| 5,616,608 | 4/1997 | Kinsella et al. | 514/449 |
| 5,620,738 | 4/1997 | Fan et al. | 427/2.3 |
| 5,624,411 | 4/1997 | Tuch | 604/265 |
| 5,626,862 | 5/1997 | Brem et al. | 424/426 |
| 5,637,113 | 6/1997 | Tartaglia et al. | 623/1 |
| 5,651,986 | 7/1997 | Brem et al. | 424/484 |
| 5,674,192 | 10/1997 | Sahatjian et al. | 604/28 |
| 5,674,241 | 10/1997 | Bley et al. | 606/198 |
| 5,674,242 | 10/1997 | Phan et al. | 606/198 |
| 5,679,400 | 10/1997 | Tuch | 427/2.14 |
| 5,697,967 | 12/1997 | Dinh et al. | 623/1 |
| 5,700,286 | 12/1997 | Tartaglia et al. | 623/1 |
| 5,702,754 | 12/1997 | Zhong | 427/2.12 |
| 5,709,874 | 1/1998 | Hanson et al. | 424/423 |
| 5,712,326 | 1/1998 | Jones et al. | 523/105 |
| 5,716,981 | 2/1998 | Hunter et al. | 514/449 |
| 5,733,925 | 3/1998 | Kunz et al. | 514/449 |
| 5,739,237 | 4/1998 | Russell et al. | 526/277 |
| 5,755,769 | 5/1998 | Richard et al. | 623/11 |
| 5,776,184 | 7/1998 | Tuch | 623/1 |
| 5,779,732 | 7/1998 | Amundson | 606/198 |
| 5,837,008 | 11/1998 | Berg et al. | 623/1 |
| 5,902,332 | * 5/1999 | Schatz | 623/1.16 |
| 5,957,975 | * 9/1999 | Lafont et al. | 623/1.38 |
| 5,972,027 | * 10/1999 | Johnson | 623/1.39 |
| 5,977,163 | * 11/1999 | Li et al. | 514/449 |
| 6,099,561 | * 8/2000 | Alt | 623/1.44 |
| 6,099,562 | * 8/2000 | Ding et al. | 623/1.46 |
| 6,099,563 | * 8/2000 | Zhong | 623/1.46 |
| 6,120,536 | * 9/2000 | Ding et al. | 623/1.43 |

FOREIGN PATENT DOCUMENTS

| | | |
|---|---|---|
| 0 439 908 A1 | 8/1991 | (EP) . |
| 0 470 246 B1 | 2/1992 | (EP) . |
| 0 470 569 A1 | 2/1992 | (EP) . |
| 0 480 809 A2 | 4/1992 | (EP) . |
| 0 480 809 A3 | 4/1992 | (EP) . |
| 0 543 653 A1 | 5/1993 | (EP) . |
| 0 551 182 A1 | 7/1993 | (EP) . |
| 0 567 816 A1 | 11/1993 | (EP) . |
| 0 568 310 A1 | 11/1993 | (EP) . |
| 0 592 870 A1 | 4/1994 | (EP) . |
| 0 604 022 A1 | 6/1994 | (EP) . |

| | | |
|---|---|---|
| 0 611 576 A1 | 8/1994 | (EP) . |
| 0 623 354 A1 | 11/1994 | (EP) . |
| 0 706 376 B1 | 4/1996 | (EP) . |
| 0 737 703 A2 | 10/1996 | (EP) . |
| 0578998B1 * | 12/1997 | (EP) .................................. 623/1.46 |
| 1 435 797 A1 | 10/1973 | (GB) . |
| 2 128 500 A1 | 5/1984 | (GB) . |
| WO 90/01969 A1 | 3/1990 | (WO) . |
| WO 90/13332 A1 | 11/1990 | (WO) . |
| WO 91/00163 A1 | 1/1991 | (WO) . |
| WO 91/07154 A1 | 5/1991 | (WO) . |
| WO 91/10424 A1 | 7/1991 | (WO) . |
| WO 91/11193 A1 | 8/1991 | (WO) . |
| WO 91/12779 A1 | 9/1991 | (WO) . |
| WO 92/00747 A1 | 1/1992 | (WO) . |
| WO 92/09073 A1 | 5/1992 | (WO) . |
| WO 92/12717 A2 | 8/1992 | (WO) . |
| WO 92/15286 A1 | 9/1992 | (WO) . |
| WO 93/06792 A1 | 4/1993 | (WO) . |
| WO 93/11120 A1 | 6/1993 | (WO) . |
| WO 94/21308 A1 | 9/1994 | (WO) . |
| WO 95/03795 A1 | 2/1995 | (WO) . |
| WO 96/03092 A1 | 2/1996 | (WO) . |
| WO 96/03984 A1 | 2/1996 | (WO) . |
| WO 96/25176 A1 | 8/1996 | (WO) . |
| WO 96/26689 A1 | 9/1996 | (WO) . |
| WO 98/29140 A1 | 7/1998 | (WO) . |
| WO 98/29141 A1 | 7/1998 | (WO) . |
| WO 98/36784 A1 | 8/1998 | (WO) . |
| WO 98/56312 | 12/1998 | (WO) . |
| WO 99/21908 | 5/1999 | (WO) . |

OTHER PUBLICATIONS

Cox, David A., M.D. et al., "Effect of Local Delivery of Heparin and Methotrexate on Neointimal Proliferation in Stented Porcine Coronary Arteries", *Cornary Artery Disease,* vol. 3, No. 3, Mar. 1992, pp. 237–248.

Cox, D. A. et al., "Local Delivery of Heparin and Methotrexate Fails to Inhibit In Vivo Smooth Muscle Cell Proliferation", *Supplement to Circulation Abstracts From the 64th Scientific Sessions,* vol. 84, No. 4, Abstract No. 0284, 1991, p. II–71.

Dev, V. et al. "Kinetics of Drug Delivery to the Arterial Wall Via Polyurethane Coated Removable Nitinol Stent–Comparative Study of 2 Drugs", *Circulation Abstract From the 66th Scientific Sessions,* vol. 88, No. 4, Part 2, Abstract No. 1657 (1993) p. I–3.

Esquivel, Carlos O., M.D. et al., "Reduced Thrombogenic Characteristics of Expanded Polytetrafluorethylene and Polyurethane Arterial Grafts After Heparin Bonding," *Surgery,* Jan. 1984, pp. 102–107.

Guyton, John R. et al., "Inhibition of Rat arterial Smooth Muscel Cell Prolicferation by Heparin," *Circulation Research,* vol. 46, No. 5, May 1980, pp. 625–634.

Jampel, Henry D., M. et al., "In Vitro Release of Hydrophobic Drugs From Polyanhydride Disk", *Ophthalmic Surgery,* dated prior to Jan. 8, 1991.

Kawahito, Koji et al., "Heparin Coated Percutaneous Cardiopulmonary Support for the Treatment of Circulatory Collapse After Cardiac Surgery," *ASAIO Journal* vol. 40, No. 4, Oct.–Dec. 1994, pp.972–976.

Kishida, Akio et al., "Immobilization of Human Thrombomodulin onto Biomaterials," *ASAIO Journal, Slide Forum— Materials 4* (1994) pp. M840–M845.

Lambert, T. et al., "A New Method For Arterial Drug Delivery Via Removable Stent", *JACC,* vol. 21, No. 2, Abstract No. 834–2 (1993) p. 483A.

Lambert, T. et al., "Localized Arterial Drug Delivery From a Poloymer Coated Removable Metallic Stent: Kinetics and Bioactivity of Forskolin", *Circulation Abstracts From the 66th Scientific Sessions,* vol. 88, No. 4, Part 2, Abstract No. 1659 (1993) p. I–3.

Linhardt, Robert J. et al., "Differential Anticoagulant Activity of Heparin Fragments Prepared Using Microbil Heparinase," *Journal of Biological Chemistry,* vol. 257, No. 13, Jul. 10, 19xx, pp. 7310–7313.

Miyama, Hajime et al., "A New Antithrombogenic Heparinized Polymer," *J. Biomed Mater. Res.,* vol. 11 (1977) pp. 251–265.

Moses, Marsha A. et al., *Inhibitors of Angiogenesis,* Review, The Children's Hospital Medical Center, Boston, MA, dated prior to Jan. 8, 1999.

Nichols, Allen B. et al., "Effect of Heparin Bonding on Catheter–induced Fibrin Formatioin and Platelet Activation," *Circulation,* vol. 70, No. 5, Nov. 1984, pp. 843–850.

Pitt, C.G. et al., "The Design of Controlled Drug Delivery Systems Based on Biodegredable Polymers", *Progress in Contraceptive Delivery Systems,* M T P Press, Lancaster, vol. 1 (1980) pp. 17–18.

Shepeck, Richard A. et al., "Examination of the Roles of Glycoprotein Ib and Glycoprotein IIb/IIIa in Platelet Deposition on an Artificial Surface Using Clinical Antiplatelet Agents and Monoclonal Antibody Blockade," *Blood,* vol. 78, No. 3, Aug. 1, 1991, pp. 673–680.

Tang, Chris et al., "Regression of Collagen–Induced Arthritis with Taxol, A Microtubule Stabilizer", *Arthritis Rheum.,* vol. 36, No. 9 (Suppl.) (1993) p. 42.

"A Powerful Case For LOPID", Parke–Davis, dated prior to Jan. 8, 1999.

Whitborne, Richard, Ph.D., Presentation at the 2nd International Coronary Stenting Summit (Mar. 1–2 1991).

Wilson, Dr. Joseph, "Thromboresistant Plastic Coating Treatment," *Research Partners, Inc.* Internet Article dated Jan. 21, 1991, 2 pages.

* cited by examiner

STENT COATING

FIELD OF THE INVENTION

The present application is generally related to medical devices. More specifically, the present invention relates to stent coatings capable of releasing agents over time. In particular, the present invention includes a blend of two co-polymers adapted to release restenosis-inhibiting agents over a sustained time period.

BACKGROUND OF THE INVENTION

Vascular disease is a leading cause of death and disability in the developed world. In the United States, more than half of all deaths are due to cardiovascular disease. Atherosclerosis is the most common form of vascular disease and leads to insufficient blood supply to body organs, which can result in hearts attacks, strokes, and kidney failure. Atherosclerosis is a form of vascular injury in which the vascular smooth muscle cells in the artery wall undergo hyperproliferation and invade and spread into the inner vessel lining, which can make the vessels susceptible to complete blockage when local blood clotting occurs. This can lead to death of the tissue served by that artery. In the case of a coronary artery, this blockage can lead to myocardial infarction and death.

Coronary artery blockage can be treated with coronary artery bypass surgery and/or angioplasty. Both procedures may initially appear to be successful, but can be in effect undone by the effect of restenosis, or the recurrence of stenosis after such a treatment. Restenosis is believed to include hyperproliferation of vascular smooth muscle cells. In particular, about one third of patients treated using angioplasty have restenosis and blockage within 6 months after the procedure.

To prevent vessel blockage from restenosis, stents are used. Stents are nominally tubular structures and can have either solid walls or lattice like walls, and can be either balloon expandable or self-expanding. After angioplasty balloon dilatation, the previously constricted vessel is at least temporarily widened. A stent can be delivered on a catheter and expanded in place or allowed to expand in place against the vessel walls. With the stent in place, restenosis may or may not be inhibited, but the probability and/or degree of blockage is reduced due to the structural strength of the stent opposing the inward force of any restenosis. Restenosis may occur over the length of the stent and be at least partially opposed by the stent. Restenosis may also occur past the ends of the stent, where the inward forces of the stenosis are unopposed.

Therapeutic agents to inhibit restenosis have been used with varying success. Taxol, an antimicrotubule agent isolated from the bark of the western Pacific Yew tree, is especially effective in inhibiting some cancers and is believed to be effective in combating restenosis. Systemic administration of Taxol can have undesirable side effects, making local administration a preferred mode of treatment.

Local administration of Taxol may be more effective when carried out over a longer time period, such as a time period at least matching the normal reaction time of the body to the angioplasty. At the same time, it may be desirable to provide an initial high dosage of Taxol over an initial period. Local administration of Taxol over a period of days or even months may be most effective in inhibiting restenosis.

Controlled release of therapeutic agents can utilize various technologies. Devices are known having a monolithic layer or coating incorporating a heterogeneous solution and/or dispersion of an active agent in a polymeric substance, where the diffusion of the agent is rate limiting, as the agent diffuses through the polymer to the polymer-fluid interface and is released into the surrounding fluid. In some devices, a soluble substance is also dissolved or dispersed in the polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically have the active agent physically immobilized in the polymer. The active agent can be dissolved and/or dispersed throughout the polymeric material. The polymeric material is often hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

What would be desirable is a stent coating capable of releasing a therapeutic agent over a sustained time period. What would be advantageous is a stent coating able to release an agent over approximately the same time period as the need for the therapeutic agent. A method for controlling the dosage rate and period of an active agent by controlling the composition of a stent coating would also be advantageous.

SUMMARY OF THE INVENTION

The present invention includes a stent having a stent body, a coating disposed over at least a portion of the body, and an active agent releasably dispersed in at least part or portion of the coating. A preferred active agent is paclitaxel, analogues, derivatives, and combinations thereof. The coating can include a blend of a first co-polymer having a first, high release rate and a second co-polymer having a second, lower release rate relative to the first release rate. The first and second copolymers are preferably erodible or biodegradable. In one embodiment, the first copolymer is more hydrophilic than the second copolymer. In one embodiment, the first copolymer includes a polylactic acid/polyethylene oxide (PLA-PEO) copolymer and the second copolymer includes a polylactic acid/polycaprolactone (PLA-PCL) copolymer.

The relative amounts and dosage rates of active agent delivered over time can be controlled by controlling the relative amounts of the faster releasing polymers relative to the slower releasing polymers. For higher initial release rates the proportion of faster releasing polymer can be increased relative to the slower releasing polymer. If most of the dosage is desired to be released over a long time period, most of the polymer can be the slower releasing polymer. The stent can be coated by spraying the stent with a solution or dispersion of polymer, active agent, and solvent. The solvent can be evaporated, leaving a coating of polymer and active agent. The active agent can be dissolved and/or dispersed in the polymer. In some embodiments, the co-polymers can be extruded over the stent body.

In use, the stent can be put into position in a body vessel such as a coronary vessel after a procedure such as angioplasty. The stent can be left in position, and the erodible or biodegradable coating allowed to degrade. As the polymeric coating degrades, the active agent can absorb into the vessel walls.

DETAILED DESCRIPTION OF THE INVENTION

The present invention includes a stent having a polymeric coating for delivering a biologically active agent or other therapeutic substance over a target time period. The polymeric coat includes a first polymer and a second polymer, where the first polymer alone would release the active agent at a faster rate than the second polymer would alone, and thus, deplete the active agent immobilized by the first polymer in a shorter time relative to the second polymer. In preferred embodiments, the first polymer is hydrophilic and the second polymer is hydrophobic.

Figure 1:
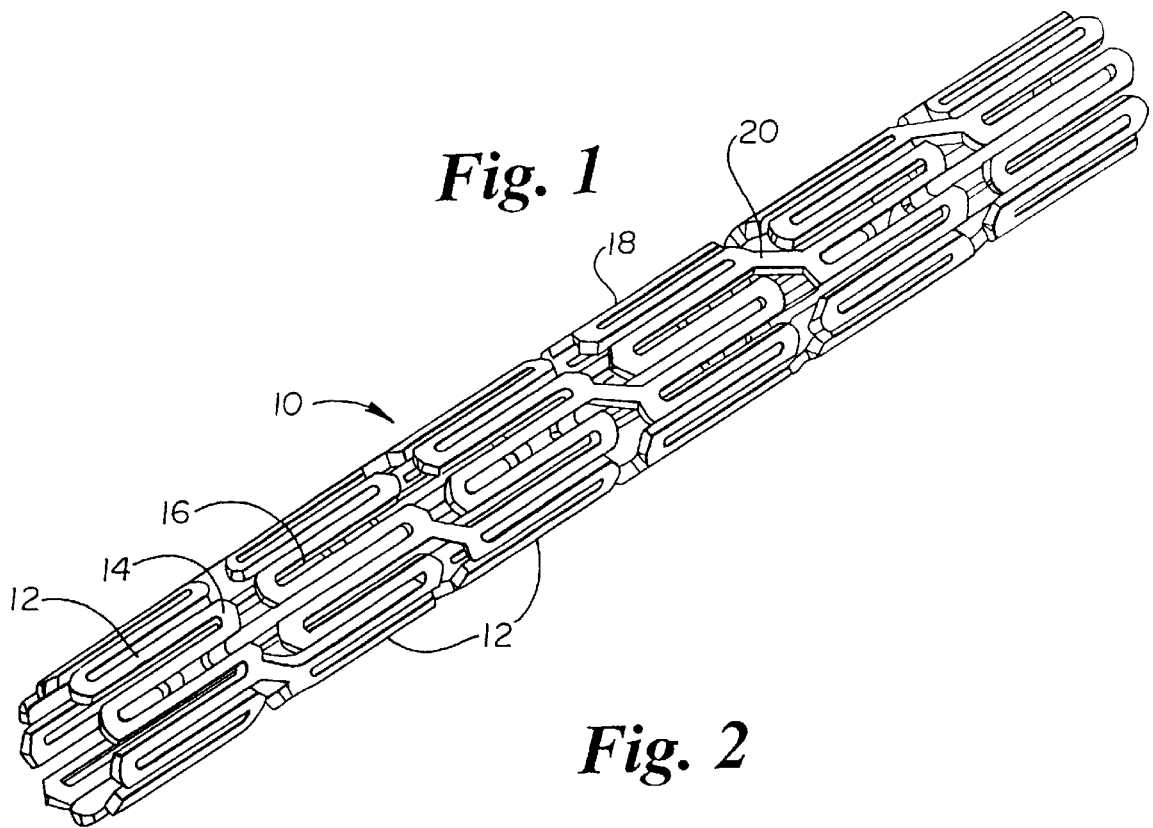
FIG. 1 is a perspective view of a stent in accordance with an exemplary embodiment of the present invention.

Referring now to the drawings wherein like reference numerals refer to like elements throughout the several views, FIG. 1 shows a perspective view of a stent 10, in a non-expanded form, in accordance with the present invention. The skeletal frame of the stent 10 preferably includes wire-like members 12 forming a distinct, repetitive serpentine pattern. This repetitive serpentine pattern consists of multiple U-shaped curves 14. The areas within the U-shaped curves 14 are open 16. With no recognizable beginning or end to this serpentine pattern, wire 12 forms expandable serpentine element 18. Serpentine elements 18 are arranged along the longitudinal axis of the stent 10 so that the U-shaped curves 14 of abutting serpentine elements 16 may be joined through an interconnecting element 20. Through the interconnecting elements 20, a continuous wire 12 framework is created between multiple serpentine elements 18 forming the stent 10.

Figure 2:
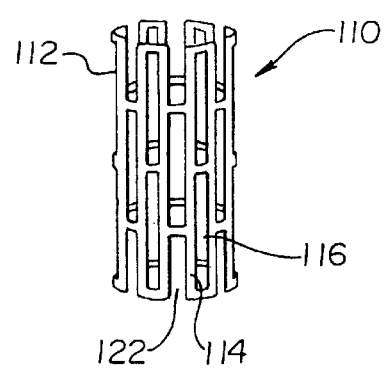
FIG. 2 is a perspective view of a further preferred stent in accordance with the present invention.

FIG. 2 shows a perspective view of a further preferred stent 110 in accordance with the present invention. This stent 110, also has a continuous wire 112 framework. This framework, however, is maintained by a repetitive rectangular-patterned element 114. The areas within the rectangular wire element 114 are open 116. The rectangular wire elements 114 are aligned lengthwise in the longitudinal axis of the stent 110. Adjacent rectangular wire elements 114 are offset half the lengthwise distance of a similar rectangular wire element 114. The end of the stent is formed by the full completion of one rectangular wire element 114, and the subsequent open end of the adjacent rectangular wire element 122. Thus, the ends of the stent possess an alternating open-closed wire configuration.

These stents are exemplary of stents which may incorporate the present invention. These, and other suitable stents are disclosed in U.S. patent application Ser. No. 08/874,190, filed Jun. 13, 1997, entitled "Polymeric Layered Stent", of which the disclosure is incorporated herein by reference.

The term "wire", as used in describing the frame material, should not be mistaken as being limited to metallic materials. In fact, the "wire" forming the stents 10 & 110 may consist of any biocompatable material possessing the structural and mechanical attributes necessary for supporting a diseased vessel. Thus, both metallic and polymeric materials are suitable. Examples of preferred biocompatable metallic materials include stainless steel, tantalum, nitinol, and gold. Preferred polymeric materials may be selected from the list immediately below, which is not exhaustive:

poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), elastin polypeptide co-polymer, polyurethane, polysiloxane and their copolymers.

The skeletal framework of the stents may be formed through various methods as well. The framework may be welded, molded, or consist of filaments or fibers which are wound or braided together in order to form a continuous structure.

Often it is beneficial to both stent and treat the localized area of a diseased vessel. A therapeutic agent, therefore, can be incorporated into a polymer and applied to the stent 10 as a polymeric surface treatment. The incorporation of a therapeutic agent into a surface treatment greatly enhances the scope of this medical device by transforming the stent into a drug-delivery system. Drugs and treatments which utilize anti-thrombogenic agents, anti-angiogenesis agents, anti-proliferative agents, growth factors, and radiochemicals may be readily deployed from within the matrix of the polymeric surface treatment. Specific examples of preferred therapeutic agents include angiopeptin, colchicine, lovastatin, trapidil, ticlopidine, hirudin, Taxol, heparin, and growth factors VEGF, TGF-beta, IGF, PDGF, and FGF.

Figure 3:
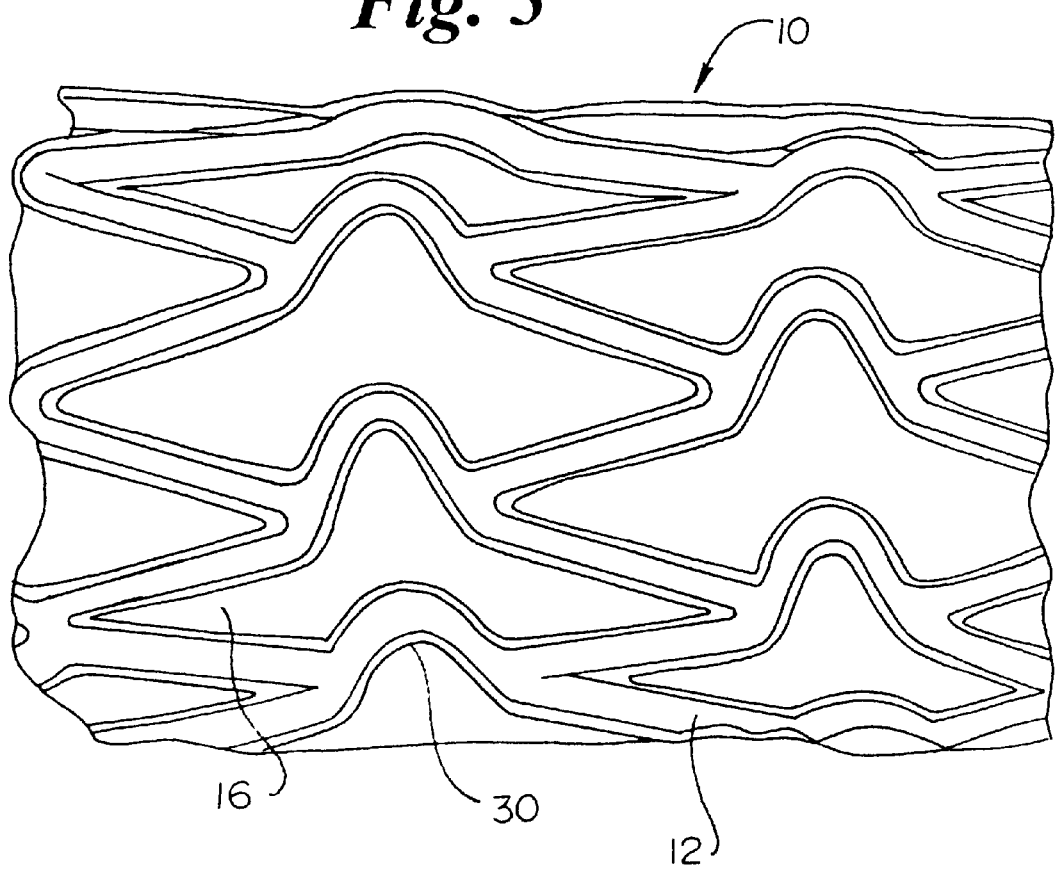
FIG. 3 is a magnified, partial plan view of the stent of FIG. 1, illustrating the polymeric coating of the present invention disposed thereon.

The application of such a surface treatment is generally accomplished through either a dipping or spraying process. For either process, a solvent carrier is preferred in order to incorporate the therapeutic agent within the polymer matrix. The applied mixture preferably comprises a solvent, a polymer, and a therapeutic agent, with subsequent evaporation of the solvent to leave a polymeric coating 30 as depicted in FIG. 3.

As previously stated, the present invention is directed to a polymeric coating incorporating a releasable therapeutic agent, wherein upon implantation the rate and duration of the agent is controlled to selected parameters which optimize treatment. It has been found that selected ratios of a mixture of a hydrophilic polymer and a hydrophobic polymer provide desired control of drug release.

In a preferred embodiment, the hydrophilic polymer includes a co-polymer of polylactic acid (PLA) and polyethylene oxide (PEO). In a preferred embodiment, the second polymer includes a co-polymer of polylactic acid (PLA) and poly(caprolactone) (PCL). The PLA-PEO copolymer is hydrophilic and erodes faster relative to a similar hydrophobic polymer in the body environment where the coated stent is positioned. The PLA-PCL copolymer is hydrophobic, and degrades more slowly than a comparable hydrophilic polymer. In a preferred embodiment, the polymer coating is formed of a blend of PLA-PCL and PLA-PEO. In preferred embodiments, the hydrophilic polymer has a molecular weight of greater than about 10,000 (Mn) and the second polymer has a molecular weight of greater than about 20,000 (Mn).

Formation of PLA-PEO copolymers is well known to those skilled in the art. See for example, U.S. Pat. Nos. 5,476,909 and 5,548,035, herein incorporated by reference. Formation of PLA-PCL copolymers is also known to those skilled in the art. See for example, U.S. Pat. No. 5,470,829, herein incorporated by reference.

One preferred embodiment includes about 20% by weight PLA-PEO and about 80% by weight PLA-PCL copolymers. Another embodiment includes about 50% by weight PLA-PEO copolymer and about 50% by weight PLA-PCL copolymer. The embodiment having about 20% PLA-PEO and 80% PLA-PCL delivers the active agent over a longer time period, but with a lower initial release, relative to the embodiment having the 50%/50% PLA-PEO/PLA-PCL combination. The relative amounts of PLA-PEO and PLA-PCL can be adjusted to achieve the desired combination of high initial dosage rate and subsequent lower but longer lasting dosage rate.

In one preferred embodiment, the active agent or therapeutic substance is a restenosis-inhibiting agent. A preferred restenosis-inhibiting agent includes a microtubule stabilizing agent such as Taxol, paclitaxel, analogues, derivatives, and mixtures thereof. For example, derivatives believed suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

The Taxol can be dissolved or dispersed in the polymeric materials and the polymeric materials adhered to the stent body. In embodiments having a blended combination of PLA-PEO and PLA-PCL, the polymeric combination can be sprayed, dipped or extruded onto the stent.

The polymeric coating of the present invention can be used with various stents. A preferred use for the coating is for coronary stents. The stents can be used following angioplasty to inhibit restenosis. The stent body can serve to hold the vessel open against any restenosis and to deliver the restenosis-inhibiting agent. In one embodiment, the coating is substantially continuous over the stent body. In another embodiment, the coating is primarily over the stent structure but not over the apertures. For example, in a stent formed of a wire mesh, the coating can closely adhere to the wires without covering the apertures therebetween.

In use, a stent according to the present invention can be selected according to desired release dosage profile and provided to the treating physician. After an angioplasty procedure, the coated stent having the restenosis-inhibiting active agent can be delivered to the stenosed, recently dilated coronary artery region. Delivery can be accomplished using methods well known to those skilled in the art, such as mounting the stent on an inflatable balloon disposed at the distal end of a catheter. With the stent advanced into position near the dilated region, the stent can be forced outward and into position against the inner vessel walls. If the stent is self-expanding, the stent can be delivered by deploying the stent from within a delivery device, allowing the stent to expand against the inner vessel walls. The active agent, as it is released from the eroding polymeric coating, can be absorbed by the inner vessel walls. Over time, the polymeric coating is eroded by bodily fluids.

Numerous advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The inventions's scope is, of course, defined in the language in which the appended claims are expressed.

What is claimed is:

1. A stent comprising:
    a stent body;
    a coating disposed over at least a portion of said body; and
    a biologically active agent dispersed in said coating, wherein said coating includes a mixture of a first co-polymer and a second co-polymer, wherein said first co-polymer releases said agent at a first rate and said second co-polymer release said agent at a second rate, wherein said second rate is slower than said first rate, such that said agent is released from said coating at a rate slower than said first rate and faster than said second rate.

2. A stent as recited in claim 1, wherein said first co-polymer is hydrophilic.

3. A stent as recited in claim 1, wherein said second co-polymer is hydrophobic.

4. A stent as recited in claim 1, wherein said first co-polymer is hydrophilic and said second co-polymer is hydrophobic.

5. A stent as recited in claim 1, wherein said first co-polymer include s PLA-PEO.

6. A stent as recited in claim 1, where said second co-polymer includes PLA-PCL.

7. A stent as recited in claim 1, wherein said first co-polymer includes PLA-PEO and said second co-polymer includes PLA-PCL.

8. A stent as recited in claim 7, wherein said agent includes an agent selected from the group consisting of paclitaxel, paclitaxel analogues, paclitaxel derivatives, and combinations thereof.

9. A stent for controllably releasing a biologically active agent over a long time period comprising:
    a stent body;
    a biologically active agent; and
    means for adhering said agent to said stent body and controllably releasing said agent from said stent body over time, wherein said means for controllably releasing said agent includes an admixture of a first means for releasing said agent at a first rate over a first time period and second means for releasing said agent at a second rate over a second time period, wherein said first rate is faster than said second rate and said first period is shorter than said second period.

10. A stent as recited in claim 9, wherein said first means for releasing includes a bioabsorbable polymeric material and second means for releasing includes a bioabsorbable polymeric material, wherein said first means is absorbed faster than said second means.

11. A stent for releasing a biologically active agent inside the human body comprising:
    a stent body;
    a polymeric coating disposed over at least a part of said stent body; and
    a biologically active material admixed with said polymeric coating, wherein said polymeric coating includes a blend of a PLA-PEO copolymer and a PLA-PCL copolymer.

12. A stent as recited in claim 11, wherein said biologically active agent includes an agent selected from the group consisting of paclitaxel, paclitaxel analogues, paclitaxel derivatives, and combinations thereof.

13. A method for inhibiting restenosis comprising the steps of:

providing a stent including a coating having a blend of a PLA-PEO copolymer and a PLA-PCL copolymer, wherein said coating includes a restenosis inhibiting agent selected from the group consisting of paclitaxel, paclitaxel analogues, paclitaxel derivatives, and combinations thereof mixed therein, such that said agent is released over a time period longer than would be released by said PLA-PEO copolymer alone, and released over a time period shorter than would be released PLA-PCL copolymer alone.

* * * * *